United States Patent
Uchida et al.

(10) Patent No.: US 10,912,516 B2
(45) Date of Patent: Feb. 9, 2021

(54) LIVING BODY INFORMATION MEASUREMENT DEVICE, LIVING BODY INFORMATION MEASUREMENT METHOD, AND STORAGE MEDIUM STORING PROGRAM

(71) Applicant: Panasonic Corporation, Osaka (JP)

(72) Inventors: Shinji Uchida, Osaka (JP); Koichi Kusukame, Nara (JP); Shinichi Shikii, Nara (JP); Masatsugu Niwayama, Shizuoka (JP)

(73) Assignee: PANASONIC CORPORATION, Osaka (JP)

( * ) Notice: Subject to any disclaimer, the term of this patent is extended or adjusted under 35 U.S.C. 154(b) by 1046 days.

(21) Appl. No.: 15/366,162

(22) Filed: Dec. 1, 2016

(65) Prior Publication Data

US 2017/0156673 A1   Jun. 8, 2017

Related U.S. Application Data

(60) Provisional application No. 62/263,874, filed on Dec. 7, 2015.

(30) Foreign Application Priority Data

Aug. 2, 2016 (JP) ................................ 2016-151877

(51) Int. Cl.
  *A61B 6/00* (2006.01)
  *A61B 5/00* (2006.01)
  (Continued)

(52) U.S. Cl.
  CPC .......... *A61B 5/6893* (2013.01); *A61B 5/0077* (2013.01); *A61B 5/0261* (2013.01);
  (Continued)

(58) Field of Classification Search
  None
  See application file for complete search history.

(56) References Cited

U.S. PATENT DOCUMENTS

| 5,566,673 A | 10/1996 | Shiono et al. |
| 2001/0028333 A1* | 10/2001 | Numazaki ............. G06K 9/209 345/44 |

(Continued)

FOREIGN PATENT DOCUMENTS

| CN | 103347446 A | 10/2013 |
| CN | 104684465 A | 6/2015 |

(Continued)

OTHER PUBLICATIONS

Suzuki Yasuhiro et al.,"Detection of Skin Region from Multiband Near-IR Spectral Characteristics", Electronics and Communications in Japan, vol. 92, No. 11, Oct. 7, 2009 (Oct. 7, 2009), pp. 19-27.

(Continued)

*Primary Examiner* — Joel F Brutus
(74) *Attorney, Agent, or Firm* — Greenblum & Bernstein, P.L.C.

(57) ABSTRACT

A living body information measurement device includes an illuminator that irradiates a living body with illumination light; an imaging unit that images the living body; and a computation unit that computes living body information on the basis of a difference between pixel data in an irradiation area being an area of the living body irradiated with the illumination light and pixel data in a non-irradiation area being an area of the living body not irradiated with the illumination light, included in pixel data associated with each position in an image generated by the imaging of the imaging unit.

15 Claims, 5 Drawing Sheets

(51) Int. Cl.
*H04N 5/225* (2006.01)
*A61B 5/026* (2006.01)
*H04N 5/235* (2006.01)
*G06K 9/00* (2006.01)
*G06K 9/20* (2006.01)
*A61B 5/024* (2006.01)

(52) U.S. Cl.
CPC ....... *G06K 9/00832* (2013.01); *G06K 9/2027* (2013.01); *H04N 5/2256* (2013.01); *H04N 5/2354* (2013.01); *A61B 5/024* (2013.01); *H04N 2209/047* (2013.01)

(56) References Cited

U.S. PATENT DOCUMENTS

| | | |
|---|---|---|
| 2008/0125664 A1 | 5/2008 | Sakai et al. |
| 2011/0237965 A1 | 9/2011 | Hayashi et al. |
| 2012/0150387 A1 | 6/2012 | Watson et al. |
| 2013/0329031 A1* | 12/2013 | Miura .................. G06K 9/2018 348/77 |
| 2013/0342691 A1 | 12/2013 | Lewis et al. |
| 2015/0366456 A1 | 12/2015 | Takamori et al. |
| 2016/0007865 A1 | 1/2016 | Sakata et al. |
| 2016/0228011 A1 | 8/2016 | Tsubaki |

FOREIGN PATENT DOCUMENTS

| | | |
|---|---|---|
| JP | 7-198598 A | 8/1995 |
| JP | 8-038460 | 2/1996 |
| JP | 2001-184507 | 7/2001 |
| JP | 2005-218507 | 8/2005 |
| JP | 2008-132012 | 6/2008 |
| JP | 2008-246004 | 10/2008 |
| JP | 2008-259676 | 10/2008 |
| JP | 2009-297234 | 12/2009 |
| JP | 2010-264095 | 11/2010 |
| JP | 2011-130996 | 7/2011 |
| JP | 2011-200271 | 10/2011 |
| JP | 2014-171574 | 9/2014 |
| WO | 2014/095759 A1 | 6/2014 |
| WO | 2014/128273 A1 | 8/2014 |
| WO | 2014/136027 A1 | 9/2014 |
| WO | 2014/136310 | 9/2014 |
| WO | 2014/155750 | 10/2014 |
| WO | 2015/045554 A1 | 4/2015 |

OTHER PUBLICATIONS

Chinese Search Report (English Language Translation), dated Jun. 29, 2020, for the related Chinese Patent Application No. 201610998934.8.

* cited by examiner

LIVING BODY INFORMATION MEASUREMENT DEVICE, LIVING BODY INFORMATION MEASUREMENT METHOD, AND STORAGE MEDIUM STORING PROGRAM

BACKGROUND

1. Technical Field

The present disclosure relates to a living body information measurement device etc. that measures living body information such as the pulse beat of a user.

2. Description of the Related Art

Hitherto, to provide services suitable for the physical condition, mental stress condition, skin condition, emotional condition, and so forth of a user, there have been developed various technologies which measure living body information, such as the pulse beat and blood pressure, serving as the basis of estimation on these conditions (the physical condition etc.).

For example, Japanese Patent No. 5320837 discloses a technology that calculates the pulse beat from an input image taken in a state in which part of a human body is pressed and having an amplitude value corresponding to the pulsation. Also, International Publication No. 2014/136310 discloses a technology that simultaneously images different areas of a living body in a non-contact state by using a single visible-light camera, obtains chronologically continuous image data, detects pulse waves at the different areas of the living body on the basis of changes in pixel values, and calculates a pulse wave propagation velocity from the time difference of the changes. Also, Japanese Patent No. 5195741 discloses a technology that detects the three-dimensional coordinates of a specific area of the face, detects the orientation and position of the face and body motion components of a test subject, corrects the average brightness in the specific area to the brightness corresponding to the frontal face by normalization, and obtains the heart rate. Also, Japanese Patent No. 5446443 discloses a technology that acquires temperature information of one or two or more areas of a living body, extracts a frequency band corresponding to the heart beat of the living body, and measures the heart rate. Also, Japanese Unexamined Patent Application Publication No. 2014-171574 discloses a technology that takes moving images, detects periodic vibration regarded as the respiration, and hence measures the respiration rate. Also, International Publication No. 2014/155750 discloses a technology that obtains a delay amount from the contour of the pulse wave of a first living body area and the contour of the pulse wave of a second living body area, and calculates an index relating to the blood flow. Also, Japanese Unexamined Patent Application Publication No. 2005-218507 discloses a technology that images an area from the shoulder to lower chest, and measures the expiration and inspiration of the respiration from a change in density of an imaging signal.

Also, Japanese Unexamined Patent Application Publication No. 2008-246004 discloses a technology that, to accurately detect the corneal reflection etc. without depending on the ambient optical environment, transfers an electric charge from a photoelectric conversion element while a light source is turned on in a period in which a first shutter is open, transfers an electric charge from the same photoelectric conversion element while the light source is turned off in a period in which a second shutter is open, and hence eliminates a brightness level component caused by the ambient light by using an image difference. Also, Japanese Unexamined Patent Application Publication No. 2008-259676 discloses a technology that controls a camera unit, acquires image data of the cheek in a state without irradiation by a light source unit, then acquires image data of the cheek in a state with irradiation by the light source unit, obtains the difference between the two types of image data, and estimates the health condition etc. of a user. Also, Japanese Unexamined Patent Application Publication No. 2011-200271 discloses a technology that, in a pulse wave detector, radiates light which is repeatedly turned on and off, and cancels an external light noise component by computation processing on the difference based on a signal acquired by a light receiving element while the light is turned on and a signal acquired by the light receiving element while the light is turned off. Also, Japanese Unexamined Patent Application Publication No. 2008-132012 discloses a technology that, in a pulse wave detector, causes a light emitting element to emit light by a light emitting quantity as a normal quantity, then causes the light emitting element to emit light by a light emitting quantity being ½ the normal quantity, and extracts a signal corresponding to a pulse beat component from the difference between the received signals. Also, Japanese Unexamined Patent Application Publication No. 8-38460 discloses a technology that causes reflected light coming from the brain surface and being divided into two to respectively pass through a filter that transmits only light with wavelengths near 570 nm and a filter that transmits only wavelengths near 630 nm, computes the difference between both, and measures the brain activity reflected in the hemoglobin concentration. Also, Japanese Unexamined Patent Application Publication No. 2001-184507 relates to an individual authentication device, and discloses a technology that takes images at time points at which a light source is turned on and off to separate light of a fluorescent lamp present in the indoor environment, environmental light such as natural light, and light from a light source from one another, and eliminates the environmental light by obtaining the differences among the images.

SUMMARY

In one general aspect, the techniques disclosed here feature a living body information measurement device including an illuminator that irradiates a living body with illumination light; an imaging unit that images the living body; and a computation unit that computes living body information on the basis of a difference between pixel data in an irradiation area being an area of the living body irradiated with the illumination light and pixel data in a non-irradiation area being an area of the living body not irradiated with the illumination light, included in pixel data associated with each position in an image generated by the imaging of the imaging unit.

With this disclosure, the living body information such as the pulse beat of a user can be properly measured while the influence of measurement environment is reduced without a restraint feel given to the user.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
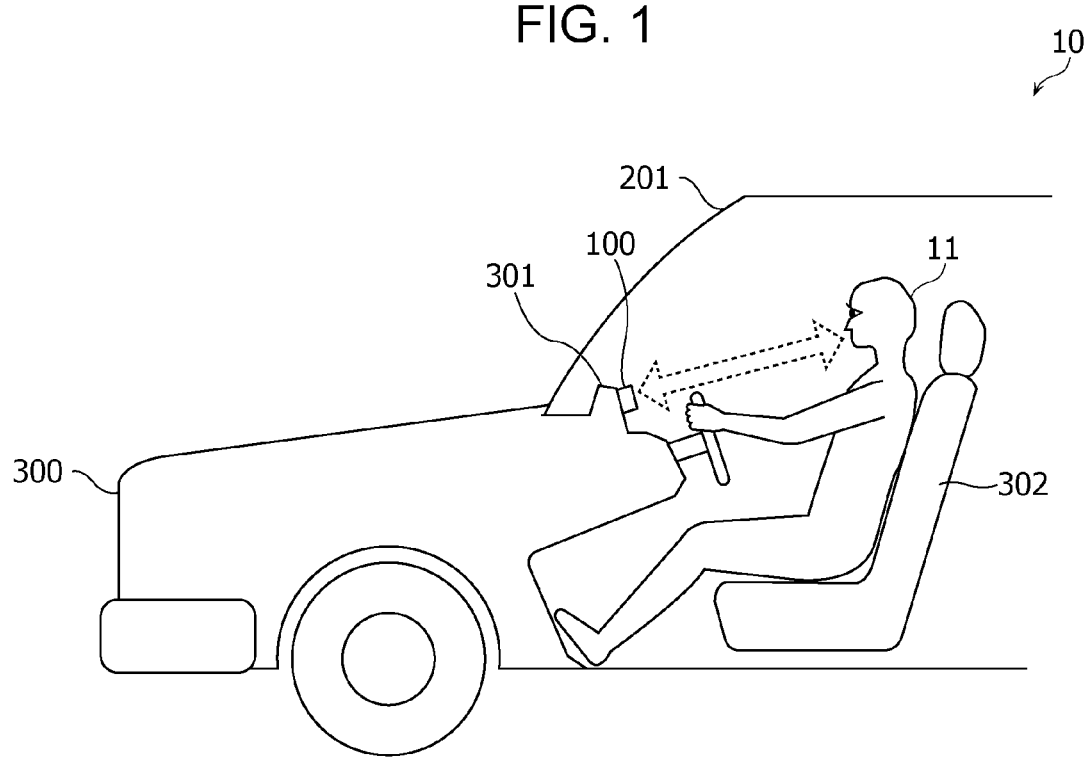
FIG. 1 is a system configuration diagram showing an example of a physical condition estimation system including a living body information measurement device according to a first embodiment.

Underlying Knowledge Forming Basis of the Present Disclosure

To provide a service suitable to the physical condition, emotional condition, etc., of a user at a proper time point, if measurement of living body information serving as the basis for estimating the physical condition, emotional condition, etc., relates to the provision of the service, it is desirable to execute the measurement, for example, while the user is driving a vehicle. In this way, to measure the living body information not at a time point at which the user lies on a bed of a hospital etc., but at a time point at which the user is in daily life such as a time point at which the user drives the vehicle, the aforementioned related art still has a margin of improvement. For example, the technology in Japanese Patent No. 5320837 that measures the blood flow by using the image taken in the state in which part of the human body is pressed has a problem of giving a restraint feel to the user. To address this problem, there is the technology of measuring the blood flow etc. by using an image taken by a camera separated from the user; however, the technology has a problem in which correct measurement is disturbed by the influences of light in the measurement environment (environmental light), vibration, etc. For example, even with the technologies in Japanese Unexamined Patent Application Publication Nos. 2008-246004, 2008-259676, and 2011-200271, the way of irradiation with the environmental light on the user (the living body) at each instant time point may vary due to vibration etc., resulting in that the measurement accuracy may be degraded.

One non-limiting and exemplary embodiment provides a living body information measurement device that may properly measure living body information such as the pulse beat of a user by a method different from those of related art in the past while the influence of the measurement environment is reduced without a restraint feel given to the user. Other non-limiting and exemplary embodiments provide a living body information measurement method that may properly measure living body information of a user while the influence of the measurement environment is reduced without a restraint feel given to the user, and a storage medium that stores a program for causing a computer to execute living body information computation processing for properly measuring living body information of a user.

A living body information measurement device according to an aspect of this disclosure includes an illuminator that irradiates a living body with illumination light; an imaging unit that images the living body; and a computation unit that computes living body information on the basis of a difference between pixel data in an irradiation area being an area of the living body irradiated with the illumination light and pixel data in a non-irradiation area being an area of the living body not irradiated with the illumination light, included in pixel data associated with each position in an image generated by the imaging of the imaging unit. Accordingly, even when the imaging is performed in a separated manner so as not to give a restraint feel to the user (the living body), the influence of the measurement environment may be reduced and the living body information may be measured.

Also, for example, the illuminator may provide the irradiation with the illumination light in an illumination form that causes a first irradiation area and a first non-irradiation area to be generated in a first local area of the living body, and causes a second irradiation area and a second non-irradiation area to be generated in a second irradiation area of the living body. For each of at least one image generated by the imaging unit, the computation unit may compute living body information relating to the first local area and living body information relating to the second local area, by calculating a difference between pixel data in the first irradiation area and pixel data in the first non-irradiation area in the image and a difference between pixel data of the second irradiation area and pixel data of the second non-irradiation area in the image, with reference to predetermined illumination pattern information indicative of the illumination form. Pixel data of an irradiation area and pixel data of a non-irradiation area in a certain image are data obtained by simultaneous imaging. Hence, even if environmental light in the measurement environment largely varies over time by vibration or other influence, the living body information may be properly measured while the influence by the environmental light is reduced. Also, the living body information computed for each local area of the living body may be used for estimation of the physical condition of the living body.

Also, the computation unit may execute predetermined statistical processing on the basis of the computed living body information relating to the first local area and the computed living body information relating to the second local area, and provides an output to the outside of the living body information measurement device in accordance with a result of the predetermined statistical processing. Accordingly, since the living body information computed for each local area of the living body is used for the predetermined statistical processing such as averaging, the living body information with increased accuracy may be output. For example, the pulsation period etc. of the blood computed from the sequentially taken image for each local area is averaged, and the heart rate etc. with high accuracy may be output. As the output, for example, displaying of the heart rate, emission of light synchronously with the heart beat, etc., may be executed.

Also, the imaging unit may include a filter having transmission characteristics for light in a predetermined wavelength band centered on 550 nm and having a width of 80 nm or smaller, and having transmission restriction characteristics for light outside the predetermined wavelength band; and an imaging element that receives light that has passed through the filter. Accordingly, the living body information relating to the blood flow may be properly measured.

Also, the computation unit may use a difference between pixel data of an irradiation area and pixel data of a non-irradiation area, included in pixel data expressing a color that satisfies a specific criterion predetermined to correspond to a skin color of a human, in an image generated by the imaging unit, as a basis of the computation of living body information. Accordingly, the influence of a part (for example, a part other than the skin of a user) unnecessary for extraction of the living body information on the user within the imaging range may be reduced, and the living body information may be accurately measured.

Also, the imaging unit may generate a color image by the imaging, and the computation unit may perform the computation of living body information on an assumption that pixel data in which a value of hue when a color is expressed in a hue-saturation-value color space is a value within a predetermined range serves as the pixel data expressing the color that satisfies the specific criterion. The color image is, for example, an RGB image. Accordingly, for example, by properly determining the predetermined range to correspond to the skin color, the living body information may be accurately measured on the basis of the pixel data imaging the skin in the image.

Also, the color image generated by the imaging unit may be configured of a plurality of pieces of pixel data two-dimensionally arranged and including data of color components of red, green, and blue. An imaging element for imaging in the imaging unit may include red, green, and blue sub-pixels configuring color pixels in which a light receiving performance of a first-color sub-pixel is 1/10 or lower a light receiving performance of a second-color sub-pixel. The first-color sub-pixel may be one of the red, green, and blue sub-pixels. The second-color sub-pixel may be one of the red, green, and blue sub-pixels and may be other than the first sub-pixel. Accordingly, when the environmental light includes the strong sunlight (the solar light), the dynamic range of the imaging element may be increased.

Also, the imaging unit may further perform the imaging by receiving light with a first wavelength and light with a second wavelength having different absorbencies by moisture. The computation unit may detect a living body estimation area being an area containing the moisture more than a predetermined level on the basis of an image generated by the imaging of the imaging unit, specify an irradiation area and a non-irradiation area from the living body estimation area, and perform the computation of living body information on the basis of pixel data of the specified irradiation area and pixel data of the specified non-irradiation area. Accordingly, the influence of a part (for example, an object around the user) unnecessary for extraction of the living body information on the user within the imaging range may be reduced, and the living body information may be accurately measured.

Also, the imaging unit may further perform the imaging by receiving infrared light. The computation unit may detect a living body estimation area being an area containing a component corresponding to the infrared light more than a predetermined threshold on the basis of an image generated by the imaging of the imaging unit, specify an irradiation area and a non-irradiation area from the living body estimation area, and perform the computation of living body information on the basis of pixel data of the specified irradiation area and pixel data of the specified non-irradiation area. Accordingly, discrimination may be possibly made between the living body and the object other than the living body by the infrared light within the imaging range, and hence the living body information may be accurately measured.

Also, the imaging unit may further measure a distance to an imaging target for each of a plurality of areas in an image generated by the imaging. The computation unit may use a difference between pixel data of an irradiation area and pixel data of a non-irradiation area, included in pixel data in which the distance measured by the imaging unit corresponds to a position in an area within a predetermined distance range in the image generated by the imaging of the imaging unit, as a basis of the computation of living body information. Accordingly, the influence of a part (for example, an object, another person, etc., located behind the user) unnecessary for extraction of the living body information on the user within the imaging range may be reduced, and the living body information may be accurately measured.

Also, the illuminator may perform the irradiation on the living body with illumination light in an illumination form that causes an irradiation area with a specific shape to be generated. For each of at least one image generated by the imaging unit, when the irradiation area with the specific shape in the image includes a center part and a peripheral part, the computation unit may perform the computation of living body information on the basis of a difference between pixel data in the peripheral part and pixel data in a non-irradiation area in the image, with reference to predetermined illumination pattern information indicative of the illumination form. Accordingly, measurement based on light passing through a tissue at a deeper position than the surface layer of the living body may be executed. In addition, for example, pixel data corresponding to the peripheral part in which the change in intensity of the illumination light is not steep with respect to the change in position as compared with the center part, and hence measurement may be accurately executed.

Also, the imaging unit may measure a distance to an imaging target for each of a plurality of areas in an image generated by the imaging. The computation unit may correct pixel data of an irradiation area and pixel data of a non-irradiation area in the image generated by the imaging of the imaging unit in accordance with the distance of the area measured by the imaging unit and corresponding to the pixel data, and then perform the computation of living body information. With this correction, the influence due to the difference in distance to the imaging object may be eliminated, and hence accurate measurement may be executed.

Also, an irradiation direction of the illumination light in the illuminator may be shifted from an optical axis of an imaging element for imaging in the imaging unit by an angle larger than a predetermined angle. Accordingly, the variation in the light quantity of the illumination light emitted on the living body due to the influence of vibration etc. may be decreased. Also, the living body information relating to an element that is displaced in the optical-axis direction of the imaging element in the living body may be properly measured.

A living body information measurement method according to another aspect of this disclosure includes irradiating a living body with illumination light; imaging the living body and hence generating an image; and computing living body information on the basis of a difference between pixel data in an irradiation area being an area of the living body irradiated with the illumination light and pixel data in a non-irradiation area being an area of the living body not irradiated with the illumination light, included in pixel data associated with each position in the image. Accordingly, the living body information may be measured while the influence of the environmental light which may vary due to vibration etc. is reduced.

Also, a non-temporary storage medium according to still another aspect of this disclosure stores a computer-readable program. The program causes the computer to execute acquiring an image generated by irradiating a living body with illumination light and imaging the living body; and computing living body information on the basis of a difference between pixel data in an irradiation area being an area of the living body irradiated with the illumination light and pixel data in a non-irradiation area being an area of the living body not irradiated with the illumination light, included in pixel data associated with each position in the image acquired in the acquiring, with reference to predetermined illumination pattern information indicative of an illumination form of the illumination light. If this program is installed in the computer, the computer functions as, for example, a part of the living body information measurement device. Accordingly, the living body information may be measured while the influence of the environmental light which may vary due to vibration etc. is reduced.

The comprehensive or specific aspects may be realized by a system, a method, an integrated circuit, a computer program, or a computer-readable storage medium, such as a CD-ROM, or may be realized by a desirable combination of the system, method, integrated circuit, computer program, and storage medium.

Embodiments of this disclosure will be described below with reference to the drawings. It is to be noted that the embodiments described below represent comprehensive or specific examples of this disclosure. The numerical values, shapes, components, arrangement of components, steps, and order of steps, etc., described in the following embodiments are merely examples, and do not limit the disclosure. Also, components not described in independent claims among the components in the following embodiments are components that may be arbitrarily added. Also, the drawings are schematic drawings, and may not provide strict illustrations.

First Embodiment

A physical condition estimation system 10 that estimates the physical condition of a user (a living body) who drives a vehicle is described below with reference to the drawings as an embodiment of the disclosure. The physical condition estimation system 10 is an example of a system including a living body information measurement device.

FIG. 1 is a system configuration diagram showing an example of the physical condition estimation system 10 including a living body information measurement device 100.

The physical condition estimation system 10 is a system that executes a living body information measurement method of measuring living body information of a user (a living body) 11 who drives a vehicle without restraining the user 11, estimates the physical condition of the user 11 on the basis of the measurement result, and provides an output corresponding to the estimation result. The physical condition in this case represents a matter that can be estimated on the basis of existing knowledge etc. with the living body information, and may be mental stress condition, skin condition, emotional condition, etc. The physical condition estimation system 10 may estimate that the physical condition of the user 11 is bad, for example, if the heart rate acquired as living body information is markedly high. If the physical condition is bad, the condition is not suitable for continuation of the driving. Hence, the physical condition estimation system 10 may output a message that recommends the user 11 to park the vehicle and take a break.

As shown in FIG. 1, the physical condition estimation system 10 includes the living body information measurement device 100 and other devices mounted on a vehicle 300. The vehicle 300 includes a dashboard 301, a seat 302, a windshield 201, and so forth. The living body information measurement device 100 is arranged, for example, at a part of the dashboard 301.

The living body information measurement device 100 is a device that measures living body information by imaging the skin (the face, neck, etc.) of the user (the living body) 11 who drives the vehicle 300. The living body information measurement device 100 is arranged separately from the surface of the living body, images the living body 11, and computes living body information on the basis of the image generated by the imaging. For example, the blood flowing in the living body 11 appears in the image of the skin. The living body information measurement device 100 analyzes the image sequentially acquired by the imaging, and hence may compute living body information (the heart rate etc.) relating to the pulsation of blood. The living body information measurement device 100 may be arranged at a desirable position as long as the living body information measurement device 100 can image the skin of the living body 11 in the vehicle 300. The position of the living body information measurement device 100 is not limited to the dashboard 301, and may be arranged at the ceiling part or door part of the vehicle 300. Also, for example, the living body information measurement device 100 may be arranged to image the face, neck, etc., not from the direct front of the face, neck, etc., of the living body 11, but from a front side obliquely shifted to the lateral side. The physical condition estimation system 10 estimates the physical condition by using a computer or the like arranged inside or outside the living body information measurement device 100 on the basis of the living body information measured by the living body information measurement device 100. The physical condition estimation system 10 outputs a message that recommends the user to take a break in accordance with the estimation result of the physical condition by sound from a loudspeaker, or an image on an instrumental panel at the dashboard 301.

Figure 2:
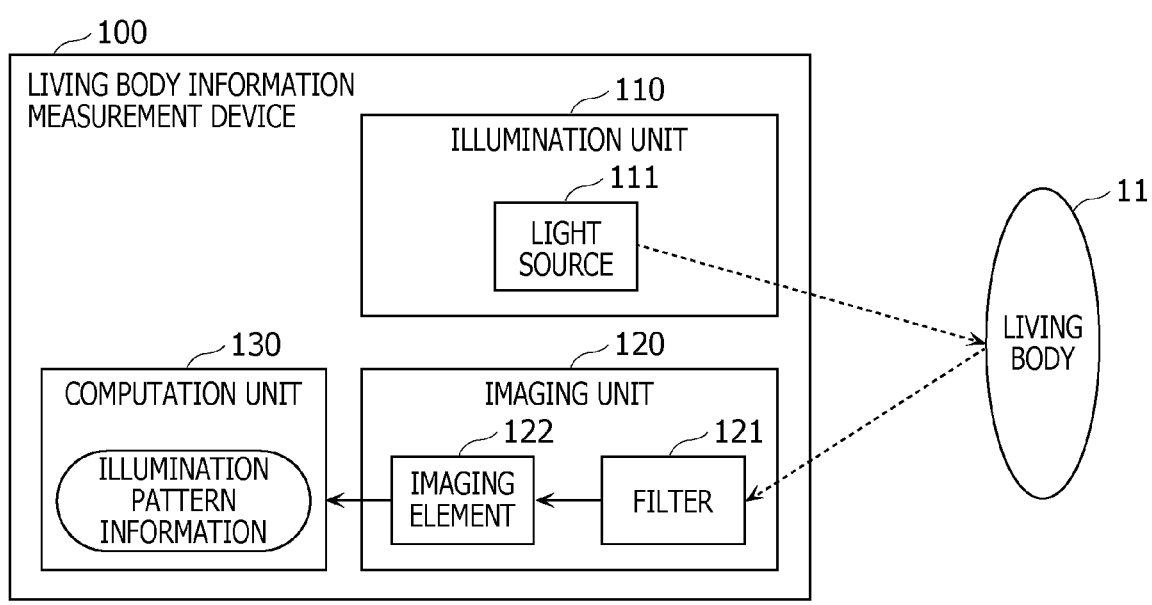
FIG. 2 is a functional block diagram of the living body information measurement device.

FIG. 2 is a functional block diagram of the living body information measurement device 100.

As shown in FIG. 2, the living body information measurement device 100 includes an illumination unit 110, an imaging unit 120, and a computation unit 130.

Figure 3:
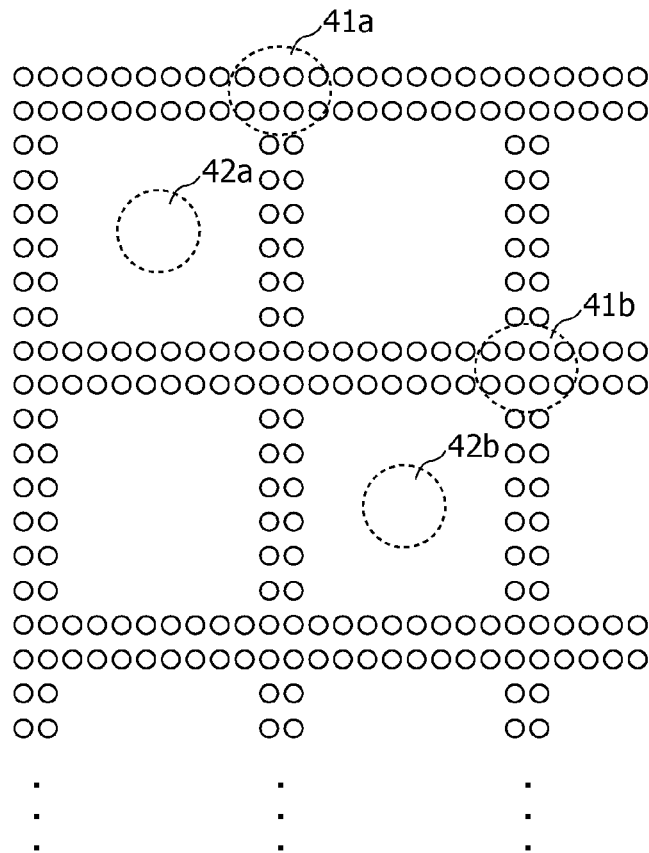
FIG. 3 is an illustration showing an example of an irradiation pattern of illumination light irradiated by the living body information measurement device according to the first embodiment.

The illumination unit 110 includes a light source 111, and irradiates the living body 11 with illumination light from the light source 111 in a predetermined illumination form (an illumination pattern). The light source 111 is, for example, one or a plurality of light emitting diodes (LEDs). FIG. 3 shows an example of an illumination pattern. In the illumination pattern of the illumination light for irradiation from the illumination unit 110, an irradiation area and a non-irradiation area are arranged in a specific layout. For example, a plurality of LEDs may be arranged in a layout of an illumination pattern (for example, at positions of circles in FIG. 3), or a light shielding film that transmits light in accordance with an illumination pattern may be arranged in front of the LEDs. The light emitted from the light source 111 is guided through, for example, optical system members (not shown), such as a lens and a mirror, in the illumination unit 110, to the living body 11 outside the living body information measurement device 100. The light source 111 may be a laser light source or the like. Preparatory adjustment (positioning or the like) is made to cause the illumination unit 110 to irradiate an imaging target area (for example, an area of the face, neck, etc.) of the user 11 with the illumination light emitted from the illumination unit 110, for example, in a state in which the user (the living body) 11 is seated on the seat 302 being the driver's seat of the vehicle 300. The user 11 may operate the adjustment. By the irradiation with the illumination light according to the illumination pattern by the illumination unit 110, the imaging target area of the user 11 seated on the seat 302 includes an irradiation area being an area irradiated with the illumination light and a non-irradiation area being an area not irradiated with the illumination light. The illumination unit 110 and the imaging unit 120 may be arranged closely to each other, or may be arranged sufficiently separately from each other at different positions in the vehicle 300. Also, the illumination unit 110 may also have, for example, a function as a display, a projector, etc., used for displaying information in the vehicle 300. The illumination form, intensity, etc., of the illumination light by the illumination unit 110 may be changed in accordance with the user (the living body) 11, the environment, etc.

The imaging unit 120 includes a filter (an optical filter) 121 and an imaging element 122, and generates an image (image data) by imaging the imaging target area (for example, the area of the face, neck, etc.) of the living body 11. The image generated by the imaging unit 120 is, for example, a color image (an RGB image) configured of a plurality of pieces of pixel data including data of color components of red (R), green (G), and blue (B) arranged two-dimensionally. The pixel data of the color image is configured of, for example, 10-bit R-component data, 10-bit G-component data, and 10-bit B-component data. If the bit depth is 8 bits, the image contrast of only 256 levels can be expressed. Hence, it may be occasionally difficult to detect the pulse wave relating to the blood flow of the living body. It is found through an experiment that the pulse wave relating to the blood flow can be measured with a high signal to noise (S/N) ratio if the bit depth is 10 bits. The bit depth of 10 bits is an example. The bit depth may be increased as 12 bits, 16 bits, etc., or is not necessarily limited to 10 bits or larger. Also, according to an experiment, the S/N ratio is degraded if the number of pixels is several tens of pixels, and the S/N ratio is high if the number of pixels is, for example, 100×100 pixels or more. Also, the imaging unit 120 sequentially takes images and sequentially generates images, for example, at 30 frames per second (FPS). The imaging unit 120 may take images at higher speed, for example, at 116 FPS.

The imaging element (a camera) 122 is configured of a charge-coupled device (CCD) image sensor, a complementary metal-oxide-semiconductor (CMOS) image sensor, or the like.

Figure 4:
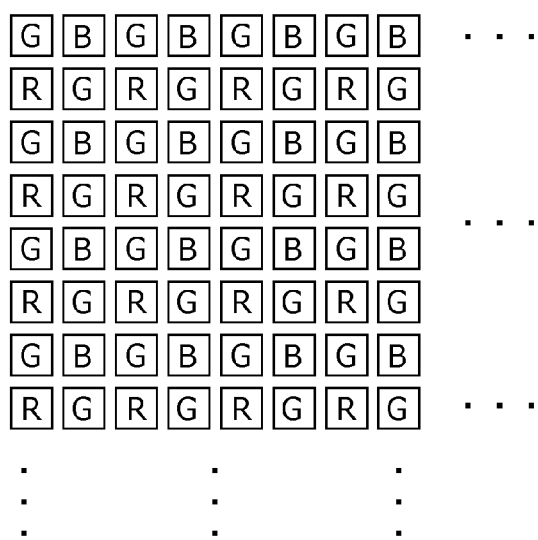
FIG. 4 is a schematic configuration diagram showing a configuration example of an imaging unit of the living body information measurement device according to the first embodiment.

In the imaging element 122, two-dimensionally arranged pixels are configured of, for example, sub-pixels each including a two by two matrix of pixels. Filters of the colors of R, G, and B (RGB filters) are respectively applied to the sub-pixels in Bayer pattern as shown in FIG. 4. The imaging element 122 receives light through the filters. In a case in which the imaging target is irradiated with strong light such as the sunlight as the environmental light, if a camera with a narrow dynamic range is used, signals are saturated, and it may be difficult to detect weak living body signals from the image. Although it is not essential, to increase the dynamic range of the imaging element (the camera) 122, the imaging element 122 may include red, green, and blue sub-pixels configuring color pixels in which the light receiving performance of a first-color sub-pixel is $1/10$ or lower the light receiving performance of a second-color sub-pixel. This configuration can be realized, for example, by decreasing the transmittance of only the light of the blue (B) color filter to $1/10$ or lower (for example, $1/1000$) among the RGB filters, or by arranging an optical filter that decreases the transmittance of only blue (B) but does not substantially decrease the transmittance of red (R) or green (G), on the front surface of the imaging element 122. Alternatively, the transmittances may be desirably adjusted. For example, the green (G) color filter may be left unchanged, the transmittance of the light of the blue (B) color filter may be decreased to $1/1000$, and the transmittance of the red (R) color filter may be decreased to $1/100$. Although it is not essential, it is effective to cause the irradiation direction of the illumination light in the illumination unit 110 to be shifted from the optical axis of the imaging element 122 by an angle larger than a predetermined angle (for example, 5°). This is because a variation in light quantity by the influence of the vibration may be increased if the irradiation direction of the illumination light is aligned with the optical axis of the imaging element 122.

When the imaging element 122 images the living body 11, the imaging element 122 receives part or the entirety of incident light on the living body information measurement device 100 (including light reflected from the living body 11) through the filter 121. The imaging element 122 receives the light that has passed through the filter 121.

Figure 5:
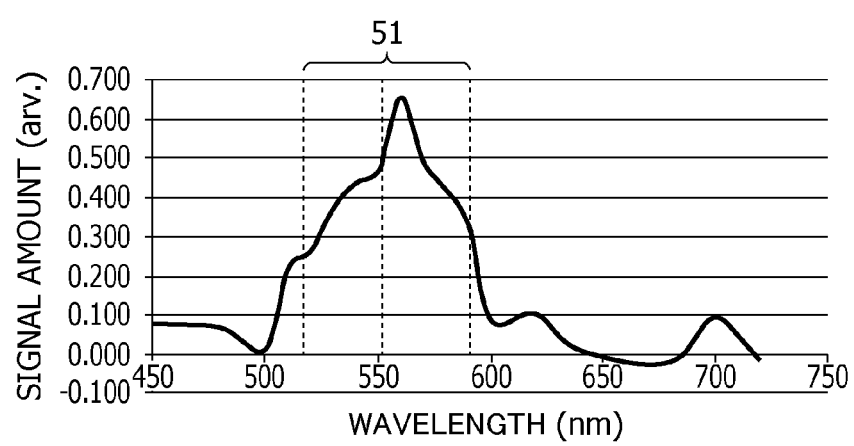
FIG. 5 is an illustration for explaining characteristics of a filter of the imaging unit of the living body information measurement device according to the first embodiment.

The filter 121 is a narrow-band color filter that has transmission characteristics (for example, the optical transmittance is a half value (50%) or higher of the maximum) for light in a predetermined wavelength band centered on a wavelength of 550 nm and having a width of 80 nm or smaller, and has transmission restriction characteristics (for example, the optical transmittance is lower than 50%) for light outside the predetermined wavelength band. FIG. 5 is a graph showing the relationship between the amplitude of the pulsation of blood analyzed from an image generated by imaging a living body, and the wavelength of the light irradiated on the living body at imaging and reflected from the living body, obtained through an experiment. FIG. 5 plots respective wavelengths of light along the horizontal axis, and signal amounts arv (average real variability) indicative of the amplitude of the pulsation of blood acquired by imaging along the vertical axis, on the basis of experimental results. In this experiment, as shown in FIG. 5, the inventors of this disclosure found that the signal amount arv has the maximum steep peak near the wavelength of 550 nm and is markedly decreased at wavelengths of 500 nm and 600 nm. The signal amount arv is largely affected by the skin tissue, for example, the melanin pigment concentration, skin moisture, blood, and surface roughness of the skin of the living body. In particular, the signal amount arv significantly relates to the absorption characteristics of the blood of the skin. It is to be noted that, as the imaging target area, similar experimental results were obtained in any part of the face, neck, submental part, arm, and palm. Also, in case of different colors of skin of living bodies (for example, different races), similar experimental results were obtained. A wavelength band 51 in FIG. 5 is a band of 550 nm±40 nm (from 510 nm to 590 nm). In the wavelength band 51, the signal amount indicative of the amplitude of the pulsation of blood is sufficiently larger than those of the other bands. A typical camera of related art receives light from 466 nm to 692 nm. In contrast, the imaging unit 120 of the living body information measurement device 100 has the filter 121 with regard to the experimental result shown in FIG. 5. With the filter 121, the living body information measurement device 100 can increase the S/N ratio of signals, and accurately measure the living body information (for example, the heart rate, pulse wave, etc.) relating to the pulsation of blood. Referring to the experimental result in FIG. 5, the filter 121 having the transmission characteristics for the above-described predetermined wavelength band (the wavelength band 51) is particularly effective; however, it is also effective to use, for example, a filter having transmission characteristics for light with wavelengths from 500 nm to 650 nm but having transmission restriction characteristics for light with the other wavelengths, instead of the filter 121. If the imaging element 122 sufficiently receives light with wavelengths shorter than 500 nm and light with wavelengths from 650 nm to 700 nm, the dynamic range of the camera may be narrowed. Also, without limiting to the replacement of the filter 121, it is effective to replace the light source 111 of the illumination unit 110 with an LED or the like that emits light having a wavelength distribution in the wavelength band 51. The light source 111 is still effective even if the light source 111 is a laser light source that emits light with a single wavelength in the wavelength band 51. However, the wavelength distribution of the light source 111 of the illumination unit 110 may not be particularly limited. Also, the filter 121 may be removed from the imaging unit 120. For example, in a dark environment, if the light source 111 that emits light with a wavelength distribution in the wavelength band 51 is used, the S/N ratio of the image by the imaging can be increased, and the living body information can be accurately measured.

The computation unit 130 analyzes the image generated by the imaging of the imaging unit 120, computes the living body information, and provides an output based on the computed living body information. The computation unit 130 is realized by, for example, a computer including a processor (a microprocessor), a memory, etc. The computer may include a storage medium such as a hard disk in addition to the memory. To be specific, for example, the processor executes a program stored in the memory, executes information processing such as living body information computation processing, and hence realizes the function of the computation unit 130. The computation unit 130 realized by the processor that executes the program sequentially acquires images sequentially generated by the imaging unit 120, stores the images in the storage medium, for example, the memory (or the hard disk), and executes living body information computation processing etc. on the basis of the images. Computing the living body information by the computation unit 130 represents recording the living body information as the computation result in, for example, a register, or the storage medium, such as the memory or the hard disk. The memory may be a transportable non-volatile memory removably attached to the computer, such as a universal serial bus (USB) memory. In this case, the living body information stored in the storage medium such as the USB memory may be used for physical condition estimation processing etc., for example, by attaching the storage medium such as the USB memory to another computer that executes the physical condition estimation processing of estimating the physical condition of the user 11.

The computation unit 130 computes the living body information on the basis of the difference between pixel data in an irradiation area being an area irradiated with the illumination light of the living body 11 being the imaging target and pixel data in a non-irradiation area being an area not irradiated with the illumination light of the living body 11, included in pixel data associated with each two-dimensional position in an image (a plane image). In this case, the irradiation area is an area that appears in an image because the illumination light irradiated on the irradiation area of the illumination pattern by the illumination unit 110 and the environmental light are reflected by the skin of the living body 11 in a manner of diffused reflection. The environmental light is light with which the living body 11 is irradiated from the environment surrounding the living body 11 other than the living body information measurement device 100. For example, the environmental light is the sunlight coming into the vehicle 300. Also, the non-irradiation area corresponds to a non-irradiation area in the illumination pattern for the illumination light irradiated from the illumination unit 110. The non-irradiation area is an area in which the illumination light is not irradiated on the skin of the living body 11 and only the reflected light of the environmental light appears in an image. The computation unit 130 discriminates between the irradiation area and the non-irradiation area by analyzing an image (for example, image processing etc. based on the light intensity distribution), with reference to predetermined illumination pattern information indicative of the irradiation pattern (FIG. 3) of the illumination light by the illumination unit 110. For example, by adjusting the imaging direction, angle of view, and so forth of the imaging unit 120 in advance, the imaging target area (the face, neck, etc.) of the user (the living body) 11 who is driving the vehicle 300 is arranged in the range of the image generated by the imaging unit 120, and the user 11 may perform the adjustment. Accordingly, the irradiation area with the illumination light in the image obtained by the imaging is substantially constant, and the illumination area includes the reflected light of the light with the component of the illumination light by the light source 111 of the illumination unit 110. Accordingly the irradiation area and the non-irradiation area are easily discriminated from each other. For example, an image may be taken once while the environmental light such as the sunlight is prevented from entering the vehicle 300 when the vehicle 300 is parked, the rough arrangement of the irradiation area and the non-irradiation area in the image may be measured, and the measurement result may be used during traveling of the vehicle 300, to discriminate between the irradiation area and the non-irradiation area. Since the computation unit 130 computes the living body information on the basis of the difference between the pixel data of the irradiation area and the pixel data of the non-irradiation area, the influence by the environmental light the intensity of which may vary can be reduced in the computation of the living body information. The irradiation way of the environmental light to the living body 11 may vary depending on each part of the imaging target area (for example, the face, neck, etc.). Reduction of the influence by the environmental light results in increase in accuracy of the living body information computed from the image.

For a specific example of the living body information computation processing by the computation unit 130, a configuration is described in which the illumination unit 110 provides irradiation with illumination light in an illumination pattern that causes a first irradiation area (for example, an irradiation area 41a in FIG. 3) and a first non-irradiation area (for example, a non-irradiation area 42a) to be generated in a first local area of the living body 11, and causes a second irradiation area (for example, an irradiation area 41b) and a second non-irradiation area (for example, a non-irradiation area 42b) to be generated in a second local area of the living body 11. In this case, for each of images sequentially acquired from the imaging unit 120, the computation unit 130 calculates the difference between pixel data in the first irradiation area (for example, the irradiation area 41a) in the first local area in the image and the first non-irradiation area (for example, the non-irradiation area 42a) in the first local area in the image, and the difference between pixel data in the second irradiation area (for example, the irradiation area 41b) in the second local area in the image and the second non-irradiation area (for example, the non-irradiation area 42b) in the second local area in the image with reference to illumination pattern information, and thus computes living body information relating to the first local area and living body information relating to the second local area. The pixel data in each of the irradiation area and the non-irradiation area in each local area may contain a single piece of pixel data or a plurality of pieces of pixel data. Also, the number of local areas is not particularly limited. Since the local area is set to have a certain small size, the influences of the environmental light to respective positions in the local area are substantially similar to each other. Hence, it may be assumed that the conditions and characteristics at respective positions of the skin of the living body corresponding to the respective positions in the local area are also similar to one another. Hence, if the living body information is computed on the basis of the difference between the pixel data of the irradiation area and the pixel data of the non-irradiation area in the local area, the influence by the environmental light is reduced, and the living body information appearing due to the degree of reflection at the living body 11 of the illumination light irradiated from the illumination unit 110 (living body information based on the difference in absorbency with respect to the illumination light or other factor) can be accurately obtained. Also, it is effective to approximate the degree of attenuation in the intensity of light with a function from the first irradiation area (for example, the irradiation area 41a) to the first non-irradiation area (for example, the non-irradiation area 42a) and to reduce the influence of noise due to various environmental light. Further, only linearly arranged pixels may be used as a group of pixels to be approximated with a function; however, it is further effective to use pixels in two or three rows. Furthermore, if an non-irradiation area like the first non-irradiation area (for example, the non-irradiation area 42a) surrounded by the first irradiation area (for example, the irradiation area 41a) is provided, in addition to the use of the group of linearly arranged pixels for computation, it is further effective to use a group of pixels arranged at equal distances from the center point of the non-irradiation area 42a and to approximate values obtained from the distance from the center point and the group of pixels with a function.

For example, the condition of the blood of the living body appears in the difference in pixel data or the result of function approximation (for example, a coefficient or a constant term). The difference in pixel data may be computed by performing computation for each component of RGB and obtaining an average, or may be computed by obtaining a weighted average in which predetermined weights are applied to respective components of RGB. For example, the pixel data used for computing the difference may be expressed by a brightness value, and the brightness value of pixel data may be expressed by, for example, 0.299×R-component value+0.587×G-component value+0.114×B-component value.

A change over time of the difference in pixel data computed for each local area of each of sequentially acquired images associated with the time at which the image is obtained represents the pulse wave relating to the blood flow by the heart beat. Hence, the heart rate, the shape of pulse wave, etc., may be computed from the difference in pixel data. The heart rate can be computed from, for example, the pulsation period of the pulse wave. Also, a pulsation interval RRI (R-R interval) can be computed. For the computation result of the heart rate etc. computed on the basis of the difference in pixel data of each local area, a value obtained as a result that predetermined statistical processing (previously determined statistical processing) such as averaging is applied to the computation results of all local areas may be computed. For example, if respective local areas have different characteristics, conditions, etc., of the skin, averaging may decrease the influence of the difference. In statistical processing, without limiting to the computation of the average value, for example, the median value, variance, or other value may be computed. The function approximation may be expressed with, for example, a function such as light quantity $Y=aX^2+bX+c$ (X: variable indicative of distance, a, b: coefficients, c: coefficient (constant term)). If the blood flow is changed by the heart beat, the coefficients a, b, and c are changed. The change amounts are obtained, and hence the living body information of the heart rate, RRI, etc., can be measured.

The computation unit 130 may provide an output on the basis of each of the computation results. That is, the computation unit 130 may execute the predetermined statistical processing on the basis of the computed living body information relating to the first local area and the computed living body information relating to the second local area, and may provide an output to the outside of the living body information measurement device 100 in accordance with the result of the predetermined statistical processing. The computation unit 130 may output, for example, information on the heart rate, or a specific message if the heart rate exceeds a predetermined threshold. The output from the living body information measurement device 100 is realized when a certain kind of information is transmitted in a form of light, sound, etc., through a display, a loudspeaker, etc., so as to be recognized by human; or when information is transmitted to a device such as a computer.

An operation of the living body information measurement device 100 is described below with reference to FIG. 6.

Figure 6:
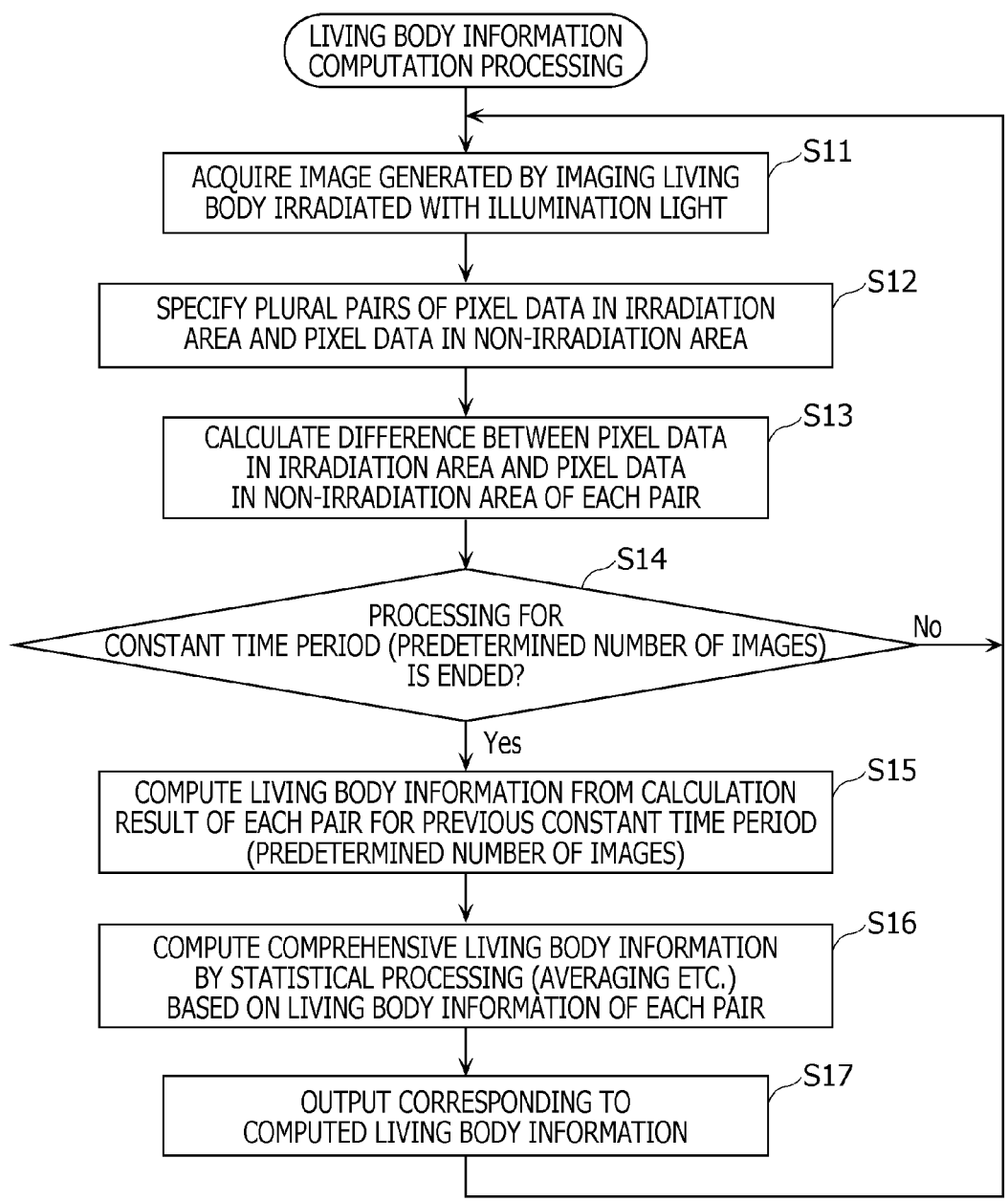
FIG. 6 is a flowchart showing an example of living body information computation processing by the living body information measurement device.

FIG. 6 is a flowchart showing an example of the living body information computation processing mainly executed by the computation unit 130 in the living body information measurement device 100.

In the living body information measurement device 100, the user (the living body) 11 who drives the vehicle 300 is irradiated with illumination light with an illumination pattern from the illumination unit 110, the imaging target area of the living body 11 is imaged by the imaging unit 120, and hence images are sequentially generated. The computation unit 130 executes, as living body information computation processing, an image acquisition step (step S11) of acquiring an image generated by irradiating the living body 11 with illumination light and imaging the living body 11, and a computation step (steps S12, S13, etc.) of computing living body information on the basis of the difference between pixel data in an irradiation area of the living body 11 and pixel data in a non-irradiation area of the living body 11, included in pixel data associated with each position in the image acquired in the image acquisition step, with reference to illumination pattern information.

The living body information computation processing is more specifically described below with reference to FIG. 6.

The computation unit 130 acquires an image generated by imaging a living body irradiated with illumination light, from the imaging unit 120 (step S11).

The computation unit 130 specifies a plurality of pairs of pixel data in an irradiation area and pixel data in a non-irradiation area in the image acquired in step S11 (step S12). For example, the computation unit 130 specifies a pair of pixel data in an irradiation area and pixel data in a non-irradiation area for each of a plurality of local areas of the living body 11. The pixel data may be a single pixel, or may be, for example, a group of a plurality of pieces of pixel data corresponding to a plurality of adjacent pixels (for example, four pixels).

Then, the computation unit 130 calculates the difference between the pixel data in the irradiation area and the pixel data in the non-irradiation area for each of the pairs specified in step S12 (S13).

Then, the computation unit 130 judges whether or not processing has been executed on a predetermined number of images (a group of images) corresponding to a constant time period (for example, several seconds, etc.) (step S14). If not, the computation unit 130 returns to step S11 for executing processing on the next image.

If it is judged in step S14 that the processing has been executed on the predetermined number of images, the computation unit 130 computes living body information from the calculation result of each pair in step S13 for the group of images (the predetermined number of images) for the immediately preceding constant time period (step S15). Accordingly, the living body information which represents the pulsation of the blood flow at the face, neck, etc., of the living body. The period, pulse beat, etc., of the pulsation of blood may be computed on the basis of the difference in pixel data for the constant time period of each pair, or for example, from the period of variation in the value of the difference in pixel data.

Then, the computation unit 130 applies the statistical processing (averaging etc.) on the living body information of each pair computed in step S15, and computes comprehensive living body information (step S16). The comprehensive living body information may be, for example, a measurement value of the pulse beat, an estimation value of the heart rate, etc.

The computation unit 130 provides an output corresponding to the living body information computed in step S16 (step S17). For example, the computation unit 130 outputs a signal indicative of the living body information to the outside of the living body information measurement device 100. A device that controls the display content on the instrumental panel, the device which has received the signal, may provide displaying corresponding to the signal. Also, the computation unit 130 may output a signal etc. indicative of a predetermined message if the living body information satisfies a certain condition (for example, if the heart rate is higher than a certain number). In step S17, the computation unit 130 may provide an output every constant time interval (for example, every several seconds, every several minutes, etc.).

After step S17, the computation unit 130 returns to step S11 again for executing the processing on the next image. Accordingly, the computation unit 130 can continuously compute the living body information and provide the output.

The physical condition estimation system 10 may estimate the physical condition of the user (the living body) 11 and may provide a service (for example, a service of recommendation to stop the user to drive when the physical condition of the user is not good) etc. corresponding to the physical condition, in accordance with the living body information computed by the living body information computation processing in the living body information measurement device 100.

Application Example

A specific application example in which the living body information measurement device 100 measures the amount of blood present in a surface layer part of the skin (blood amount) is described below. This application example is merely an example, and the living body information measurement device 100 may be applied to, for example, measurement of the pulse wave, heart beat, etc., relating to a variation over time in the blood amount.

The illumination unit 110 includes a light source 111 that emits blue (B) light with a wavelength of 450 nm, green (G) light with a wavelength of 550 nm, and red (R) light with a wavelength of 700 nm. An illumination pattern being an illumination form (an irradiation form) of illumination light from the light source 111 uses a lattice-shaped illumination pattern as shown in FIG. 3. A target area to be irradiated with the illumination light is, for example, the entirety or part of the face.

The imaging unit 120 images the entirety or part of the face as the imaging target area with a proper angle of view, and generates an RGB image including pixel data corresponding to each of pixel positions arranged two dimensionally.

The computation unit 130 references the illumination pattern for each color component of RGB of the RGB image, then discriminates between an irradiation area and a non-irradiation area on the basis of the intensity distribution of the color component of the pixel data, and extracts the difference between pixel data of the irradiation area and pixel data of the non-irradiation area for each local area with a certain size. Thus, the computation unit 130 obtains information detected almost only by the illumination light. From the detected information, the blood amount can be calculated on the basis of the difference in absorbency of light with respective wavelengths by the blood. As the result that the imaging element 122 of the imaging unit 120 detects the respective color components of R, G, and B of the RGB image, discrimination is made between light with the wavelength of 550 nm that is relatively more absorbed by the blood and light with the wavelength of 650 nm or higher that is relatively less absorbed by the blood (for example, wavelengths from 680 nm to 730 nm having flat spectral absorbency characteristics by the blood). A typical camera may include a filter for detecting, for example, light with wavelengths from 564 nm to 700 nm. However, light with wavelengths from 564 nm to 600 nm may not be desirable because such light includes information on amplitude fluctuations of the pulse wave. Hence, it is effective to use the filter that detects the light with the wavelengths from 680 nm to 730 nm as described above. Also, by previously setting the light quantity of the illumination light constant, stable measurement can be executed. Also, by previously checking the relationship of the light quantity value with respect to the blood amount by a close-contact type blood amount sensor, and by previously determining information in which the blood amount is associated with the light quantity value, the computation unit 130 can reference the information and calculate the blood amount as an absolute amount.

Second Embodiment

An embodiment in which part of the living body information measurement device 100 of the physical condition estimation system 10 described in the first embodiment is modified is described below.

A second embodiment provides an embodiment in which the computation unit 130 is modified to limit the pixel data (pixel data of an irradiation area and pixel data of a non-irradiation area) used for computation of living body information to pixel data that satisfies a certain condition. The respective components of the physical condition estimation system 10 and the living body information measurement device 100 according to this embodiment are substantially similar to those of the first embodiment, and hence are described here by using reference signs (see FIGS. 1 and 2) similar to those of the first embodiment. Points different from the first embodiment are described here, and points not described here are similar to those of the first embodiment.

The computation unit 130 of the living body information measurement device 100 according to this embodiment uses the difference between pixel data of an irradiation area and pixel data of a non-irradiation area, included in pixel data expressing a color that satisfies a predetermined specific criterion to correspond to a skin color of a human, in an image generated by the imaging unit 120, as the basis of computation of living body information. As a specific example, for example, pixel data in which, when colors expressed by pixel data of an RGB image including respective components of R, G, and B are expressed in a HSV color space including hue (H), saturation (S), and value (V) (brightness), the value of the hue (H) is within a predetermined range serves as pixel data expressing a color that satisfies specific criterion. The predetermined range is, for example, from 0° to 30° when the hue (H) is expressed in a range from 0° to 360°. Accordingly, the pixel data serving as the basis of computation of living body information may be limited to, for example, pixel data expressing a color corresponding to a skin color or pale orange. It is to be noted that the specific criterion may be limited to a certain range for a component other than the hue (H). This is merely an example, and a color that satisfies a specific criterion may be determined in accordance with, for example, the race, to fit with the skin color of the user (the living body) 11.

As described above, the computation unit 130 computes the living body information on the basis of the difference between the pixel data of the irradiation area and the pixel data of the non-irradiation area as described in the first embodiment, included in the pixel data expressing the color corresponding to the skin color of a human in the image generated by the imaging unit 120. Accordingly, the living body information that appears on the skin such as the blood flow may be accurately properly extracted while the hair, eye, background, etc., included in the image acquired by the imaging of the living body 11 are eliminated. The method of limiting the pixel data to the pixel data serving as the basis of the computation of the living body information to the aforementioned pixel data corresponding to the skin color rather than limiting it to pixel data in an area of the face by detecting the face from an image by using a face recognition technology on the basis of existing machine learning etc. is effective for measurement of living body information relating to the blood flow (the pulse wave, heart rate, etc.), moisture of skin, etc. With the existing face recognition technology, it is difficult to eliminate the hair, eye, etc., and it is difficult to recognize a partial area, such as part of the face, neck, etc. In contrast, the method of limiting the pixel data to the pixel data of the color corresponding to the skin color is effective because the hair, eye, etc., can be eliminated, and even part of the face, neck, etc., can be identified with accuracy on a pixel basis. The computation unit 130 may be applied with both the method of limiting the pixel data to the pixel data corresponding to the skin color, and the method of limiting the pixel data to the pixel data in a range of the face recognized by the existing face recognition technology.

To identify the aforementioned pixel data corresponding to the skin color of a human, the imaging unit 120 is desirable to at least take a color image. The imaging unit 120 does not have to include an RGB filter, and may be three-color separation type. For example, the imaging unit 120 may use a complementary color filter (a CMYG filter) of cyan (C), magenta (M), yellow (Y), and green (G).

Modification of Second Embodiment

A modification is described below in which the living body information measurement device 100 described in the aforementioned second embodiment is further modified to discriminate between the skin of the user (the living body) 11 who drives the vehicle 300 and the seat 302 on which the user 11 is seated.

In the second embodiment, it has been described that the pixel data which is used by the computation unit 130 as the basis of the computation of the living body information in the image has been limited to the pixel data expressing the color (for example, a skin color) that satisfies the specific criterion corresponding to the skin color of a human. However, an image taken by the imaging unit 120 may include the seat 302 (for example, a head rest part) of the vehicle 300 in addition to the skin (the face, neck, etc.) of the user (the living body) 11. If the seat 302 has a color similar to the skin color, pixel data including the seat 302 may express the color that satisfies the specific criterion.

Hence, in the living body information measurement device 100 according to this modification, the skin of the user (the living body) 11 who operates the vehicle 300 is discriminated from the sear 302 on which the user 11 is seated, by using detection of infrared light. In this modification, points different from the second embodiment are described here, and points not described here are similar to those of the second embodiment.

Figure 7:
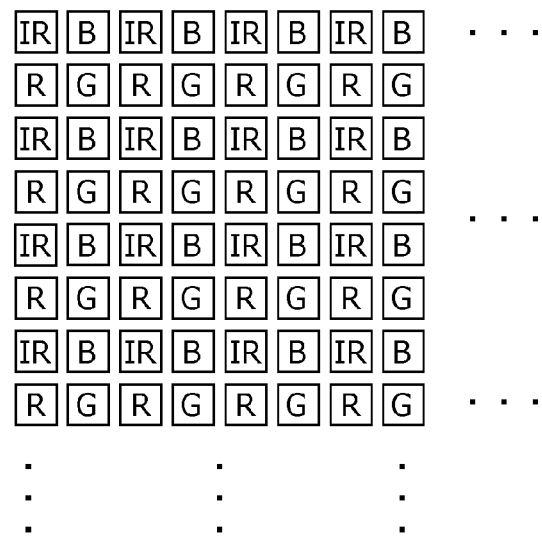
FIG. 7 is a schematic configuration diagram showing a configuration example of an imaging unit of a living body information measurement device according to a modification of a second embodiment.

The imaging unit 120 performs imaging by further receiving infrared light. For example, the imaging unit 120 performs imaging with an imaging element 122 arranged with a filter to receive a component of infrared light (InfraRed, IR) such as near-infrared light, in addition to the respective components of RGB. In the imaging element 122 according to this modification, two-dimensionally arranged pixels are configured of, for example, sub-pixels each including a two by two matrix of pixels. Filters of R, G, B, and IR are respectively applied to the sub-pixels in an arrangement as shown in FIG. 7. In the example in FIG. 7, a filter for IR and a group of filters for respective colors of R, G, and B are repetitively two-dimensionally arranged on the imaging element 122. The imaging element 122 receives light through the filters. Pixel data of an image generated by the imaging includes the respective components of RGB and the component of IR.

Also, the computation unit 130 detects a living body estimation area that is an area including IR components corresponding to the infrared light more than a predetermined threshold, on the basis of an image generated by imaging of the imaging unit 120. The living body estimation area is an area that is discriminated from an object other than a living body, and estimated as a living body. The predetermined threshold is, for example, a value predetermined on the basis of an experiment etc. to discriminate a human such as the living body 11 from an object such as the seat 302. The computation unit 130 specifies an irradiation area and a non-irradiation area in pixel data being pixel data in the detected living body estimation area and being pixel data expressing a color that satisfies the specific criterion corresponding to the skin color of a human, and computes living body information on the basis of pixel data of the specified irradiation area and pixel data of the specified non-irradiation area.

The imaging unit 120 may be provided with a light receiving element that receives infrared light in addition to the imaging element 122. In this case, the imaging element 122 generates an RGB image by imaging. The computation unit 130 may provide discrimination whether or not the area is the living body estimation area by judging whether or not the light receiving element, which detects infrared light in the same direction as the direction of the imaging element 122 in the imaging unit 120, detects infrared light with the predetermined threshold or more in each area to correspond to each area including a single or a plurality of pixels of the RGB image as a unit.

The infrared light used for the detection of the living body estimation area may be mid-infrared light (mid-infrared radiation) instead of the near-infrared light (near-infrared radiation). In this case, the computation unit 130 detects the temperature distribution by using the mid-infrared radiation, and may provide discrimination whether or not the area is the living body estimation area by judging whether or not infrared light of the threshold value or more is detected in the area, that is, whether or not the temperature distribution of a certain level or higher is detected as the living body for each area including a single or a plurality of pixels of the RGB image as a unit.

Alternatively, instead of the method of discriminating between the living body 11 and the seat 302 etc. by using the infrared light, a distance measurement method may be used in which a distance measurement device additionally provided in the living body information measurement device 100 measures the distance of an object in the angle of view imaged by the imaging unit 120, and discriminates between the living body 11 and the seat 302 on the basis of the measurement result of the distance and a predetermined upper limit value etc. (a predetermined distance range) from the distance measurement device to the living body.

When the distance measurement method is used, the imaging unit 120 of the living body information measurement device 100 further measures distances to an imaging target in a plurality of areas (areas each including a single or a plurality of pixels as a unit) in an image generated by imaging. For measurement of distances, any of existing technologies, such as time of flight (TOF) method, may be used. Also, the computation unit 130 computes living body information on the basis of the difference between pixel data of an irradiation area and pixel data of a non-irradiation area, included in pixel data being pixel data corresponding to a position in an area in which the distance measured by the imaging unit 120 is within the predetermined distance range and being pixel data expressing a color that satisfies the specific criterion corresponding to the skin color of a human, in an image generated by imaging of the imaging unit 120. The predetermined distance range may be fixed, or may be adjustable by the user (the living body) 11. With the distance measurement method, the living body 11 (for example, a user who drives the vehicle 300) being a measurement target for living body information can be properly discriminated from another living body (for example, a person seated on a rear seat). The living body 11 being the measurement target for the living body information may be discriminated from another living body by image recognition based on the shape, size, etc., of the living body appearing in an image.

Alternatively, instead of the method of discriminating between the living body 11 and the seat 302 etc. by the infrared light or instead of the distance measurement method, a moisture detection method may be used in which the living body 11 is discriminated from the seat 302 etc. by detecting the moisture in the living body.

When the moisture detection method is used, the imaging unit 120 of the living body information measurement device 100 further performs imaging by receiving light with a first wavelength and light with a second wavelength having mutually different absorbencies by moisture. For example, the light with the first wavelength is light with a wavelength (for example, 960 nm) that is largely absorbed by the moisture. In contrast, the light with the second wavelength is light with a wavelength (for example, 780 nm) that is not largely absorbed by the moisture or blood. The first wavelength and the second wavelength may be any wavelengths as long as the two wavelengths have different absorbencies by the moisture. For example, it is effective to provide a filter in the imaging unit 120, for detecting the light with the first wavelength and the light with the second wavelength in a manner discriminated from one another. For example, a group of a filter for light with the first wavelength, a filter for light with the second wavelength, and filters for respective colors of R, G, and B is repeatedly two-dimensionally arranged at the imaging element 122. Also, it is effective to provide irradiation with light (for example, near-infrared light) including the light with the first wavelength and the light with the second wavelength from the illumination unit 110 to correspond to the imaging unit 120. Also, the computation unit 130 detects a living body estimation area (that is, an area discriminated from an object etc. other than a living body and estimated as a living body) being an area containing moisture more than a predetermined level on the basis of an image generated by imaging of the imaging unit 120, specifies an irradiation area and a non-irradiation area from the living body estimation area, and computes living body information on the basis of pixel data of the specified irradiation area and pixel data of the specified non-irradiation area. The pixel data used for the computation of the living body information is pixel data expressing a color that satisfies the specific criterion corresponding to the skin color of a human. The computation unit 130 judges whether or not each of a plurality of areas (an area including a single or a plurality of pixels as a unit) in an image is an area containing the moisture more than the predetermined level, by comparing the difference in light reception quantity between the detected light with the first wavelength and the detected light with the second wavelength with the predetermined criterion value for discriminating between a living body and an object such as the seat etc. Since the living body contains moisture by a relatively large amount, with the moisture detection method, the living body 11 (for example, a user who drives the vehicle 300) being a measurement target for living body information can be properly discriminated from an object, such as plastic (synthetic resin), paper, etc., containing moisture by a relatively small amount.

Third Embodiment

An embodiment is described below, in which the processing method of a signal obtained by imaging of the imaging element 122 of the living body information measurement device 100 of the physical condition estimation system 10 described in the first embodiment is modified to reduce the influence of environmental light (external light). The respective components of the physical condition estimation system 10 and the living body information measurement device 100 according to this embodiment are substantially similar to those of the first embodiment, and hence are described here by using reference signs (see FIGS. 1 and 2) similar to those of the first embodiment. Points different from the first embodiment are described here, and points not described here are similar to those of the first embodiment.

In this embodiment, the imaging target (the face, neck, etc., of the user 11 who drives the vehicle 300) is irradiated with light sin(wt) modulated by the illumination unit 110 of the living body information measurement device 100. Then, the computation unit 130 extracts a signal relating to a change over time in pixel data from images (sequentially taken images) sequentially generated on the basis of light (feedback light) received by the imaging element 122 of the imaging unit 120.

For example, when the pulsation of the blood flow of the user (the living body) 11 is expressed as a signal S(t), a signal f1(t) relating to a change over time in pixel data to be extracted by the computation unit 130 is expressed as, for example, f1(t)=S(t)*sin(wt). The computation unit 130 further multiplies f1(t) by a signal sin(wt) with the same frequency as the frequency of the light irradiated from the illumination unit 110, and hence obtains a signal f2(t). The signal f2(t) is expressed as f2(t)=S(t)*sin(wt)*sin(wt)=S(t)*(1−cos(2 wt))/2. When an RGB image is generated by imaging of the imaging unit 120, the signal f2(t) may be obtained for each of the color components of R, G, and B. The computation unit 130 uses a low-pass filter (LPF) for the signal f2(t) and hence eliminates the component of 2 w. For example, it is effective to use a LPF or the like with a cutoff frequency of 2 Hz. The computation unit 130 eliminates a frequency component of the heart beat or higher around 60 beats per minute (BPM) from the signal f2(t) by using the LPF. Accordingly, living body information relating to the pulsation of the blood flow can be properly extracted.

In this embodiment, the example of using sin(wt) with a frequency of w is used as light modulated by the illumination unit 110 of the living body information measurement device 100; however, this is merely an example, and for example, a rectangular wave signal with a frequency w may be used.

Fourth Embodiment

An embodiment is described below, in which the computation unit 130 of the living body information measurement device 100 of the physical condition estimation system 10 shown in the first embodiment corrects pixel data of an image. The respective components of the physical condition estimation system 10 and the living body information measurement device 100 according to this embodiment are substantially similar to those of the first embodiment, and hence are described here by using reference signs (see FIGS. 1 and 2) similar to those of the first embodiment. Points different from the first embodiment are described here, and points not described here are similar to those of the first embodiment.

In this embodiment, the imaging unit 120 of the living body information measurement device 100 measures a distance to an imaging target (the face, neck, etc., of the user 11 who drives the vehicle 300) for each of a plurality of areas in an image generated by imaging. For the measurement of the distance, any of existing technologies may be used. TOF method may be used, or for example, a method of providing two imaging elements 122, imaging the living body 11 simultaneously with the imaging elements 122, and measuring the distance to the living body 11 on the basis of parallax information.

Also, the computation unit 130 corrects pixel data of an irradiation area and pixel data of a non-irradiation area in an image generated by imaging of the imaging unit 120 in accordance with the distance of the area measured by the imaging unit 120 corresponding to the pixel data, and then computes living body information on the basis of the pixel data. When the value of pixel data in an image is set to be increased as the imaging element 122 of the imaging unit 120 receives light with higher intensity, the computation unit 130 corrects the value of pixel data to be decreased as the distance is decreased. Accordingly, a measurement error due to a difference in distance from the imaging unit 120 to the face, neck, etc., of the living body 11 can be decreased.

Fifth Embodiment

An example (an application example of the living body information measurement device 100) is described below, in which the physical condition estimation system 10 described in the first embodiment is modified and living body information of the user (the living body) 11 is measured in a desirable location at a desirable time without regard to the vehicle 300. In this case, description is given with reference signs (see FIGS. 1 and 2) similar to those of the first embodiment. However, in this embodiment, the vehicle 300 may be present or may not be present. Points different from the first embodiment are described here, and points not described here are similar to those of the first embodiment.

In this embodiment, as living body information relating to a tissue at a specific depth (for example, a part deeper than the surface layer) of the skin of the living body 11, oxygen saturation (artery blood oxygen saturation), melanin amount, skin moisture, in-body moisture, dark part under eye, etc.

The illumination unit 110 of the living body information measurement device 100 includes a light source 111 that provides irradiation with pattern light having a specific shape of a line (linear) shape, an ellipsoidal shape, a circular shape, a donut-like shape, a diamond-like shape, or other shape. In this case, in particular, the shapes of ellipsoidal shape, circular shape, donut-like shape, diamond-like shape, etc., are effective. This is because, when the face is irradiated with light with such a shape, it is easy to recognize an irradiation area by comparing and verifying the irradiation point with respect to a previously set recognition pattern. In contrast, this is because when point-shaped illumination is used, if the irradiation point overlaps a mole or a macula, it is difficult to identify the irradiation point. Also, if the pattern light with the shape of ellipsoidal shape, circular shape, donut-like shape, diamond-like shape, etc., is used, the orientation of the face can be easily calculated by calculating the distortion amount with respect to the previously set recognition pattern.

In general, when the orientation of the face is changed, the distance per single pixel of a camera differs from the distance on the frontal face (the distance is changed from the distance for the frontal face). That is, as the orientation of the face is more obliquely turned, the measured distance becomes smaller. This represents that, when the intensity distribution of light entered in the living body from the irradiation point of light and fed back to the surface again is measured with the camera, the intensity distribution per pixel is substantially changed, and an error may be generated when living body information is calculated. However, if the distortion amount of the illumination light with the specific shape is obtained, the intensity distribution of light measured with the camera can be corrected into a spatial distribution amount viewed from the actual front. This can be effective.

Also, it is effective that the size of each shape is, for example, 3 mm or larger. This is because, even if a mold, a macula, etc., is present, it is easy to recognize the illumination area, and recognize the illumination area and the non-illumination area.

Also, when the feedback light from the living body is detected, it is also very effective to measure not only one side of the illumination area but also the entire surface because the signal amount can be increased.

Figure 8:
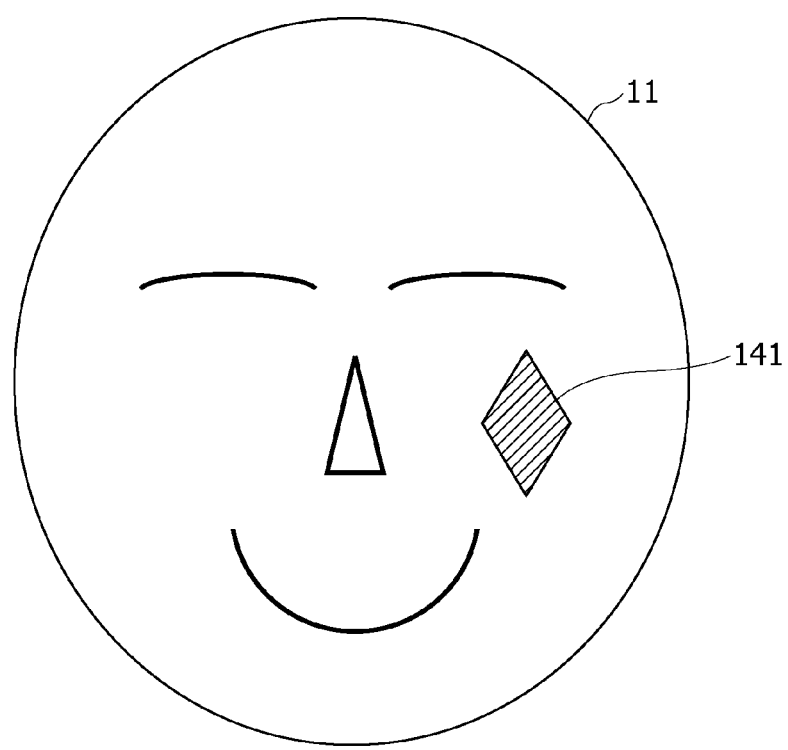
FIG. 8 is an illustration showing an example of an irradiation pattern of illumination light irradiated on a living body by a living body information measurement device according to a fifth embodiment.

The light source 111 emits, for example, light including light with a wavelength of 780 nm and light with a wavelength of 830 nm being near-infrared light; however, it is merely an effective example, and may emit light with other wavelengths. For example, near-infrared light may penetrate to a depth of several millimeters from the skin surface of a living body. The illumination unit 110 irradiates the living body 11 with illumination light in an illumination form (an illumination pattern) that generates an irradiation area with a specific shape. FIG. 8 is an illustration showing an example of an illumination pattern of illumination light irradiated from the illumination unit 110 on the living body 11 (an illumination pattern 141 with a diamond-like shape).

The imaging unit 120 sequentially generates an image by sequentially imaging an imaging target area (the face etc.) of the living body 11 irradiated with the pattern light with the specific shape by the illumination unit 110. The image is an image, such as an RGB image, generated with filters discriminating light with respective wavelength bands from one another and receiving the light. Pixel data corresponding to two-dimensional positions configuring the image include, for example, data of components with a plurality of wavelengths, such as respective color components of R, G, and B. It is effective to adjust the exposure time period for imaging by the imaging unit 120 or the intensity etc. of the illumination light by the illumination unit 110 to obtain a proper S/N ratio in living body information as the computation result by the computation unit 130.

The computation unit 130 references predetermined illumination pattern information (information indicative of a layout with a specific shape) indicative of an illumination pattern, and for each of at least one image generated by the imaging unit 120, when an irradiation area with a specific shape in the image includes a center part and a peripheral part, specifies pixel data in the peripheral part and pixel data in a non-irradiation area in the image. Then, the computation unit 130 computes living body information on the basis of the pixel data in the specified peripheral part and the pixel data in the non-irradiation area. In the example in FIG. 8, areas close to edges (four edges) of the diamond-like shape in the illumination pattern 141 with the diamond-like shape represent the peripheral part, and a part near the center of the diamond-like shape surrounded by the peripheral part represents the center part. In this way, since the computation unit 130 uses the pixel data of the peripheral part of the irradiation area with the specific shape instead of the center part, the computation unit 130 may properly extract information of a living body component of a part at a position deeper than the surface layer of the skin of the living body 11. If the skin of the living body 11 is irradiated with illumination light with a point-shaped illumination pattern, light that diffuses around the point is rapidly attenuated, and hence it may be difficult to obtain a sufficient S/N ratio. Owing to this, in the living body information measurement device 100, by using the illumination light with the above-described specific shape not being the point-like shape, and by integrating the differences between a plurality of pieces of pixel data of the peripheral part where light, which passes through the skin and is diverged, and pixel data of the non-irradiation area (for example, pixel data of the non-irradiation area near each pixel data of the peripheral part), living body information relating to a tissue at a position deeper than the surface layer of the skin is measured while the influence of the environmental light is reduced. Accordingly, the number of pixels that can be integrated is increased as compared with the point-shaped illumination pattern, and a sufficient S/N ratio can be obtained.

The computation unit 130 references a table indicative of the correlation between respective components of pixel data and oxygen saturation predetermined on the basis of an experiment etc., and computes the oxygen saturation etc., as living body information of the living body 11 in accordance with a component corresponding to each wavelength of light (for example, each of color components of R, G, and B), indicated by the difference in pixel data obtained for each of sequentially taken images. Hemoglobin in blood has different absorbencies of light with a constant wavelength of red (R) depending on whether or not the hemoglobin in blood is bonded to oxygen. For example, the computation unit 130 may compute the amount of hemoglobin (Hb) as living body information from a direct-current component without a variation over time in each of sequentially taken images.

In accordance with an item to be measured as living body information, it is effective to select proper illumination light in the living body information measurement device 100, a proper filter used in the imaging unit 120, or a component of pixel data to be used for computation by the computation unit 130. To measure the melanin amount and dark part under the eye as living body information, for example, light with a blue (B) wavelength is used in addition to the two wavelengths (780 nm and 830 nm) of the aforementioned near-infrared light. Also, to measure the skin moisture and in-body moisture, it is effective to add light with a wavelength of 960 nm that is relatively absorbed more by water. Also, the illumination pattern may be selected in accordance with an item to be measured as living body information. Also, an algorithm to be used for computing living body information by the computation unit 130 may include any of existing methods corresponding to the item to be measured as the living body information. Also, if the computation unit 130 computes the item to be measured as the living body information by weighted averaging of each component (for example, each color component of R, G, and B) of the difference in pixel data (the difference between an irradiation area and a non-irradiation area) such as an RGB image, each coefficient (a weight with respect to each component)

to be used for weighted averaging may be selected in accordance with the item to be measured. Further, the front surface of the face of the living body 11 may be scanned with illumination light that is emitted in a narrow range as a light beam or the like, and the spatial distribution of various measurement values of living body information may be obtained. When the face is scanned with the illumination light, it is effective to specify the positions of the eyes on the basis of a previously taken image of the entire face, and switches the illumination light between on (light up) and off (light out) to prevent the illumination light from entering the eyes (that is, the illumination light is turned off at the positions of the eyes).

Also, the living body information measurement device 100 may measure information relating to respiration as living body information as described below instead of measuring living body information relating to a tissue at a specific depth of the skin of the living body 11.

To measure the respiration, the illumination unit 110 of the living body information measurement device 100 irradiates a range from the neck to lower abdomen of the living body 11 (an imaging target area) with pattern light (illumination light) having a mesh-shaped illumination pattern, for example, as shown in FIG. 3. Other than the mesh shape, two or more concentric circle patterns are effective, or another shape may be employed. The irradiation direction of the illumination light by the illumination unit 110 is sufficiently shifted from the light reception direction (the optical axis) of the imaging element 122 of the imaging unit 120 (for example, by 45°). Accordingly, the detection sensitivity of the imaging element 122 for a change in position of each part of the living body 11 due to the respiration is increased. The imaging unit 120 is arranged to cause the imaging target area to be within the angle of view. The illumination unit 110 (the light source 111 etc.) is arranged at a part separated from the imaging unit 120 (the imaging element 122 etc.). The illumination unit 110 also provides irradiation with the illumination light toward the center of the imaging target area.

The illumination light irradiated from the illumination unit 110 is, for example, light with multiple colors (colors containing respective components of R, G, and B), and may be light containing an infrared radiation component. The imaging unit 120 sequentially images the living body 11, and hence sequentially generates an RGB image or an image of RGB+IR. Since the number of color components included in pixel data is increased as described above, measurement accuracy can be increased as compared with measurement with single-color light.

The computation unit 130 extracts a respiration signal from the difference between a part with a large variation and a part with a small variation on the basis of the variations at equivalent positions of parts in pixel data by an illumination pattern having a shape such as a mesh shape in pixel data of images sequentially generated by the imaging unit 120. Accordingly, the influence of vibration of the living body 11 and vibration of the environment, such as a vehicle, in which the living body information measurement device 100 is arranged, may be reduced and a respiration signal may be extracted. The computation unit 130 can compute living body information relating to the respiration, such as the respiration rate, strength, and expiration/inspiration ratio, on the basis of the respiration signal.

The living body information measurement device 100 or an external device may estimate the physical condition of the user (the living body) 11 by using existing technology, algorithm, etc., on the basis of the living body information, such as the oxygen saturation, melanin amount, skin moisture, in-body moisture, dark part under eye, respiration rate, and expiration/inspiration ratio described in the embodiments.

Other Embodiments

The first to fifth embodiments have been described above as examples of technologies relating to this disclosure. However, the above-described embodiments are merely examples, and various changes, additions, omissions, etc., can be made as a matter of course.

In the above-described first to fourth embodiments, an operation that the illumination unit 110 of the living body information measurement device 100 switches the state of the light source 111 between on (light up) and off (light out) has not been described. However, on/off of the light source 111 may be switched every constant time period (for example, every time when the imaging unit 120 images a single frame). In the imaging unit 120, gain, shutter speed, etc., are previously properly set to prevent saturation of a signal of an image obtained by imaging the living body 11 receiving illumination light irradiated when the light source 111 is on. The imaging unit 120 alternately generates an image of the living body 11 at least partly irradiated with the illumination light and an image of the living body 11 not irradiated with the illumination light at all, for example, in correspondence with the period of imaging such as 30 FPS. The computation unit 130 can reduce the influence of the environmental light by subtracting the image not irradiated with the illumination light from the image irradiated with the illumination light, and extract a signal relating to reflected light from the living body 11 for only the illumination light. The computation unit 130 computes living body information on the basis of the image obtained by the subtraction (subtraction image). Accordingly, in the living body information measurement device 100, when the living body information is computed by using the difference between the pixel data of the irradiation area and the pixel data of the non-irradiation area in the image at least partly irradiated with the illumination light, the computation result on the basis of the subtraction image may be also used. Also, by using the light source 111 that can selectively individually output light with a plurality of wavelengths, only light with a specific wavelength may be turned on and off for the switch of the light source 111 between off and on.

Also, the living body information measurement device 100 described in the above-described embodiments may be used for a system other than the physical condition estimation system 10, and may measure the living body 11 in a state before the living body 11 gets on the vehicle. Also, the part of the living body 11 imaged by the living body information measurement device 100 for measurement of living body information may be part or the entirety of the face, neck, etc., or may be the skin of other part, such as a palm or an arm.

Part or the entirety of respective components of the living body information measurement device 100 in the above-described embodiments may be configured of a single system large scale integration (LSI). The system LSI is a super multifunctional LSI manufactured by integrating a plurality of configuration units on a single chip. To be specific, the system LSI is a computer system including a microprocessor, a ROM, a RAM, etc. The RAM stores a computer program. The microprocessor operates according to the computer program, and hence the system LSI achieves the function. Also, respective units of the components configuring each of the above-described devices may be individually formed as a single chip, or formed as a single chip to include part or the entirety of the units. Also, the system LSI is exemplified here; however, it may be referred to as IC, LSI, super LSI, or ultra LSI by the difference in the degree of integration. Also, the method of integration is not limited to LSI, and the integration may be realized by a dedicated circuit or a general purpose processor. A field programmable gate array (FPGA) that is programmable after the LSI is manufactured, or a reconfigurable processor that can reconfigure connection and setting of a circuit cell in the LSI may be used. Further, if a technology of integration which replaces the LSI by the advance of semiconductor technology or other derivative technology is developed, functional blocks may be integrated by using the technology as a matter of course. Application of biological technology etc. may be one of such possibilities.

Also, part or the entirety of the respective components in the above-described embodiments may be configured of an IC card or a single module detachably attached to a device such as a computer. The IC card of the module is a computer system configured of a microprocessor, a ROM, a RAM, etc. The IC card or the module may include the above-described super multifunction LSI. The microprocessor operates according to the computer program, and hence the IC card or the module achieves the function. The IC card or the module may be tamper resistant.

Also, an aspect of this disclosure may be, for example, a living body information measurement method including the entirety or part of the procedure shown in FIG. 6. Also, the living body information measurement method may be a computer program realized by a computer (for example, a program executing the living body information computation processing including the image acquisition step and the computation step), or may be a digital signal configured of the computer program. Also, an aspect of this disclosure may be a configuration in which the computer program or the digital signal is stored in a computer-readable storage medium, for example, a flexible disk, a hard disk, a CD-ROM, a MO, a DVD, a DVD-ROM, a DVD-RAM, a Blu-ray (registered trademark) Disc (BD), or a semiconductor memory. Also, an aspect of this disclosure may be the digital signal stored in the storage medium. Also, an aspect of this disclosure may be the computer program or the digital signal that is transmitted through a telecommunication line, a wireless or wired communication line, a network represented by the Internet, data broadcast, etc. Also, an aspect of this disclosure may be a computer system including a microprocessor and a memory. The memory may store the computer program. The microprocessor may operate according to the computer program. Also, an aspect of this disclosure may be implemented by another independent computer system by storing the program or the digital signal in the storage medium and transporting the storage medium, or by transmitting the program or the digital signal via the network etc.

Also, an embodiment realized by desirably combining the respective components and functions described in the above-described embodiments is included in the scope of this disclosure.

This disclosure can be used for measuring living body information, and can be used in, for example, a physical condition estimation system etc.

What is claimed is:

1. A living body information measurement device,. comprising:
    an illuminator that irradiates a living body with illumination light;
    a camera that images the living body; and
    a processor that computes living body information on the basis of a difference between pixel data in an irradiation area being an area of the living body irradiated with the illumination light and pixel data in a non-irradiation area being an area of the living body not irradiated with the illumination light, included in pixel data associated with each position in an image generated by the imaging of the camera.

2. The living body information measurement device according to claim 1,
    wherein the illuminator provides the irradiation with the illumination light in an illumination form that causes a first irradiation area and a first non-irradiation area to be generated in a first local area of the living body, and causes a second irradiation area and a second non-irradiation area to be generated in a second irradiation area of the living body, and
    wherein, for each of at least one image generated by the camera, the processor computes living body information relating to the first local area and living body information relating to the second local area, by calculating a difference between pixel data in the first irradiation area and pixel data in the first non-irradiation area in the image and a difference between pixel data of the second irradiation area and pixel data of the second non-irradiation area in the image, with reference to predetermined illumination pattern information indicative of the illumination form.

3. The living body information measurement device according to claim 2,
    wherein the processor executes predetermined statistical processing on the basis of the computed living body information relating to the first local area and the computed living body information relating to the second local area, and provides an output to the outside of the living body information measurement device in accordance with a result of the predetermined statistical processing.

4. The living body information measurement device according to claim 1,
    wherein the camera further includes
    a filter having transmission characteristics for light in a predetermined wavelength band centered on 550 nm and having a width of 80 nm or smaller, and having transmission restriction characteristics for light outside the predetermined wavelength band, and
    an imaging element that receives light that has passed through the filter.

5. The living body information measurement device according to claim 1,
    wherein the processor uses a difference between pixel data of an irradiation area and pixel data of a non-irradiation area, included in pixel data expressing a color that satisfies a specific criterion predetermined to correspond to a skin color of a human, in an image generated by the camera, as a basis of the computation of living body information.

6. The living body information measurement device according to claim 5,
    wherein the camera generates a color image by the imaging, and
    wherein the processor performs the computation of living body information on an assumption that pixel data in which a value of hue when a color is expressed in a hue-saturation-value color space is a value within a predetermined range serves as the pixel data expressing the color that satisfies the specific criterion.

7. The living body information measurement device according to claim 6,
wherein the color image generated by the camera is configured of a plurality of pieces of pixel data two-dimensionally arranged and including data of color components of red, green, and blue,
wherein an imaging element for imaging in the camera includes red, green, and blue sub-pixels configuring color pixels in which a light receiving performance of a first-color sub-pixel is 1/10 or lower a light receiving performance of a second-color sub-pixel,
wherein the first-color sub-pixel is one of the red, green, and blue sub-pixels, and
wherein the second-color sub-pixel is one of the red, green, and blue sub-pixels and is other than the first sub-pixel.

8. The living body information measurement device according to claim 5,
wherein the camera further performs the imaging by receiving light with a first wavelength and light with a second wavelength having different absorbencies by moisture, and
wherein the processor detects a living body estimation area being an area containing the moisture more than a predetermined level on the basis of an image generated by the imaging of the camera, specifies an irradiation area and a non-irradiation area from the living body estimation area, and performs the computation of living body information on the basis of pixel data of the specified irradiation area and pixel data of the specified non-irradiation area.

9. The living body information measurement device according to claim 5,
wherein the camera further performs the imaging by receiving infrared light, and
wherein the processor detects a living body estimation area being an area containing a component corresponding to the infrared light more than a predetermined threshold on the basis of an image generated by the imaging of the camera, specifies an irradiation area and a non-irradiation area from the living body estimation area, and performs the computation of living body information on the basis of pixel data of the specified irradiation area and pixel data of the specified non-irradiation area.

10. The living body information measurement device according to claim 5,
wherein the camera further measures a distance to an imaging target for each of a plurality of areas in an image generated by the imaging, and
wherein the processor uses a difference between pixel data of an irradiation area and pixel data of a non-irradiation area, included in pixel data in which the distance measured by the camera corresponds to a position in an area within a predetermined distance range in the image generated by the imaging of the camera, as a basis of the computation of living body information.

11. The living body information measurement device according to claim 1,
wherein the illuminator performs the irradiation on the living body with illumination light in an illumination form that causes an irradiation area with a specific shape to be generated, and
wherein, for each of at least one image generated by the camera, when the irradiation area with the specific shape in the image includes a center part and a peripheral part, the processor performs the computation of living body information on the basis of a difference between pixel data in the peripheral part and pixel data in a non-irradiation area in the image, with reference to predetermined illumination pattern information indicative of the illumination form.

12. The living body information measurement device according to claim 1,
wherein the camera measures a distance to an imaging target for each of a plurality of areas in an image generated by the imaging, and
wherein the processor corrects pixel data of an irradiation area and pixel data of a non-irradiation area in the image generated by the imaging of the camera in accordance with the distance of the area measured by the camera and corresponding to the pixel data, and then performs the computation of living body information.

13. The living body information measurement device according to claim 1,
wherein an irradiation direction of the illumination light in the illuminator is shifted from an optical axis of an imaging element for imaging in the camera by an angle larger than a predetermined angle.

14. A living body information measurement method, comprising:
irradiating a living body with illumination light;
imaging the living body and hence generating an image; and
computing living body information on the basis of a difference between pixel data in an irradiation area being an area of the living body irradiated with the illumination light and pixel data in a non-irradiation area being an area of the living body not irradiated with the illumination light, included in pixel data associated with each position in the image.

15. A non-temporary storage medium storing a computer-readable program,
wherein the program causes the computer to execute:
acquiring an image generated by irradiating a living body with illumination light and imaging the living body; and
computing living body information on the basis of a difference between pixel data in an irradiation area being an area of the living body irradiated with the illumination light and pixel data in a non-irradiation area being an area of the living body not irradiated with the illumination light, included in pixel data associated with each position in the image acquired in the acquiring, with reference to predetermined illumination pattern information indicative of an illumination form of the illumination light.

* * * * *